US005635644A

United States Patent [19]
Ishikawa et al.

[11] Patent Number: 5,635,644
[45] Date of Patent: Jun. 3, 1997

[54] APPARATUS FOR MEASURING A LAYER THICKNESS USING TRANSVERSE WAVES OF ULTRASONIC WAVES

[75] Inventors: Kohichi Ishikawa, Kakogawa; Hitoshi Utsumi, Kobe, both of Japan

[73] Assignee: Shinkokensa Service Kabushiki Kaisha, Hyogo-ken, Japan

[21] Appl. No.: 502,975

[22] Filed: Jul. 17, 1995

[30] Foreign Application Priority Data

Jul. 26, 1994 [JP] Japan .................................. 6-174310
Mar. 14, 1995 [JP] Japan .................................. 7-054648

[51] Int. Cl.$^6$ ................................................ G01N 29/10
[52] U.S. Cl. ......................... 73/614; 73/622; 73/644; 73/615
[58] Field of Search ........................... 73/597, 644, 602, 73/610, 613, 614, 615, 622, 620, 606, 627, 598, 629, 642; 128/660.06, 662.03

[56] References Cited

U.S. PATENT DOCUMENTS

| | | |
|---|---|---|
| 3,538,752 | 11/1970 | Weinbaum .............................. 73/615 |
| 4,088,028 | 5/1978 | Hildebrandt ........................... 73/611 |
| 4,213,184 | 7/1980 | Fasching ............................... 364/574 |
| 4,398,420 | 8/1983 | Haesen et al. ......................... 73/597 |
| 4,624,127 | 11/1986 | Narushima et al. .................. 73/1 DV |
| 4,953,405 | 9/1990 | Hara et al. ............................. 73/602 |
| 4,991,440 | 2/1991 | Pleinis et al. .......................... 73/615 |
| 5,009,103 | 4/1991 | Sato et al. ............................. 73/597 |
| 5,201,225 | 4/1993 | Takahashi et al. ..................... 73/615 |

FOREIGN PATENT DOCUMENTS 0167418   7/1991   Japan .................................. 73/615

*Primary Examiner*—Hezrone E. Williams
*Assistant Examiner*—Rose M. Miller
*Attorney, Agent, or Firm*—Jordan and Hamburg

[57] ABSTRACT

An apparatus which measures a thickness of a layer using transverse waves of ultrasonic waves, and includes: a sensor unit having a probe for obliquely transmitting and receiving to and from the surface of a material to be measured having first and second layers with different acoustic impedances in a depth direction: an extractor for extracting, from a wave reception signal representing waves received by the probe, reflected waves from a boundary between the first and the second layers of the material; and a calculator for calculating a distance between the surface of the material and the boundary.

19 Claims, 13 Drawing Sheets

REFLECTION TIME

FIG. 11
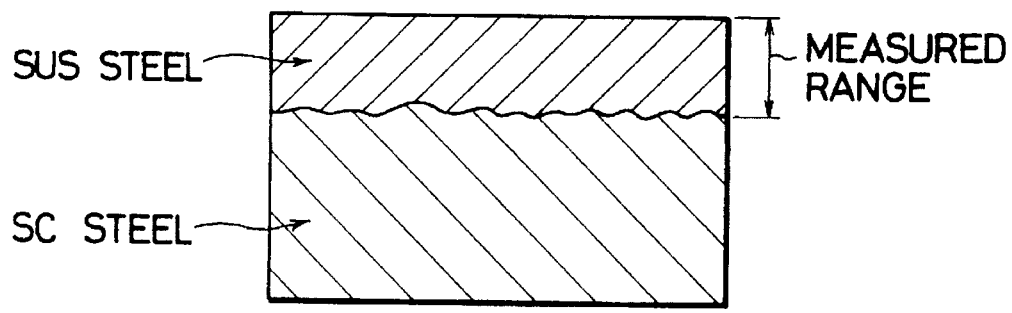
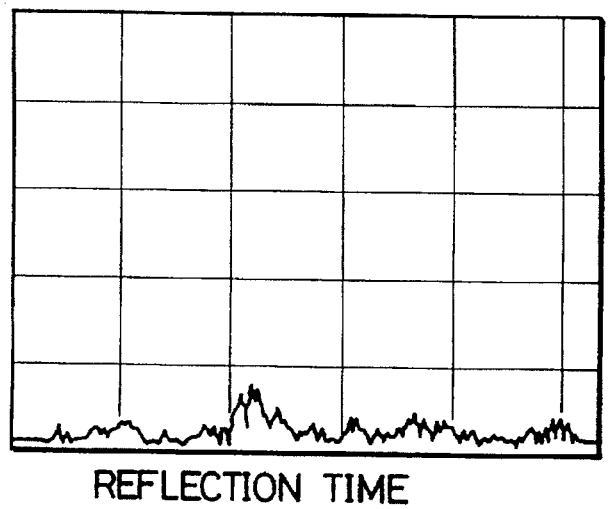
FIG. 12
REFLECTION TIME
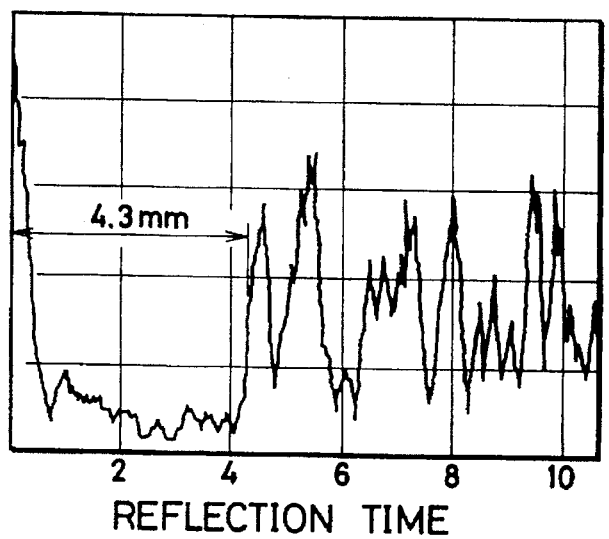
FIG. 13
REFLECTION TIME

APPARATUS FOR MEASURING A LAYER THICKNESS USING TRANSVERSE WAVES OF ULTRASONIC WAVES

BACKGROUND OF THE INVENTION

This invention relates to an apparatus for measuring a thickness of a hard layer formed by hardening and a thickness of a buildup of a material different from a base material in a non-destructive manner using transverse waves of ultrasonic waves.

Generally, members which tend to be strongly abraded when gears, rolls or the like are used have their surfaces hardened in order to reduce abrasion as much as possible, thereby forming hard layers on their surfaces. An accurate grasp of a thickness of the hard layer is a very critical matter to be checked in view of guarantee of the quality of the abrasive members and their estimated lives.

A conventional method for measuring the thickness of the hard layer is, for example, such that the hard layer is cut in its depth direction and the cut surface is macroscopically observed after being abraded and etched, and that the thickness of the hard layer is grasped by measuring hardness at several points on the cut surface. However, this method requires much labor in order to measure the hardness and necessitates a destructive examination, thus a random examination. Measurement costs are also tremendously expensive.

As a countermeasure, a method using ultrasonic waves has been used to measure the thickness of the hard layer. This method employs water immersion or local water immersion to improve a measurement accuracy. An example of the use of water immersion to measure the thickness of the hard layer is disclosed in Japanese Unexamined Patent Publication No. 3-130658.

A variety of flaw detection probes used in association with the local water immersion have been proposed. These probes include a probe holder for setting a probe at a desired distance in water from a material to be measured (disclosed in Japanese Unexamined Utility Model Publication No. 3-81553), a flaw detection probe which has a water bag before a sensing surface and a friction resistant contact film on a contact surface of the water bag with a material to be measured to prevent a water leak (disclosed in Japanese Unexamined Utility Model Publication No. 2-67259), and a probe shoe capable of adjusting a distance in water by moving a probe and a material to be measured and adjusting the sensitivity, and of detecting a flaw on a curved surface such as of a pipe (disclosed in Japanese Unexamined Utility Model Publication No. 57-116863).

The flaw detection probe disclosed in the Japanese Unexamined utility Model Publication No. 2-67259 transmits ultrasonic waves in such a manner that their transverse waves are obliquely incident upon the material to be measured. It has been known that the use of the transverse waves of the ultrasonic waves is effective in detecting a defect in a welded portion of a plate and detecting the depth of a crack on the surface.

However, the transverse waves of the ultrasonic waves employed in a variety of conventional apparatuses are limitedly used to detect a flaw such as an internal defect or a crack. These apparatuses do not actively use the transverse reflected waves caused by an irregular reflection (diffusion) produced in a grain boundary in order to obtain the measurement result, but rather eliminate the reflected wave as noises.

SUMMARY OF THE INVENTION

It is an object of the present invention to provide a layer thickness measuring apparatus which has overcome the problems and drawbacks residing in the prior art.

It is another object of the present invention to provide a layer thickness measuring apparatus which actively employs transverse waves reflected because of an irregular reflection produced in a grain boundary to measure a thickness of a hard layer formed on a material, a thickness of a buildup of a material different from a base material, etc.

Accordingly, the invention is directed to an apparatus for measuring a thickness of a layer, comprising a sensor unit including a probe for obliquely transmitting and receiving to and from the surface of a material to be measured having first and second layers with different acoustic impedances in a depth direction; an extractor which extracts, from a wave reception signal representing waves received by the probe, reflected waves from a boundary between the first and the second layers of the material; and a calculator which calculates a distance between the surface of the material and the boundary.

In this apparatus, the probe is inclined at a specified angle with respect to the measurement surface of the material to be measured, and the ultrasonic pulse having a frequency lying in the MHz range is transmitted. Since the ultrasonic waves are obliquely transmitted to the material, the transverse waves as well as the longitudinal waves propagate in the material. Because the transverse waves have a shorter wavelength than the longitudinal waves, the irregular reflection of the transverse waves is larger than that of the longitudinal waves, thereby largely reflecting the influence of different materials in the grain boundary. When the ultrasonic waves strike against the grain particles, the transverse and longitudinal waves thereof are reflected by the boundary while their modes are transformed. A relatively large portion of the transverse wave components return along a path of incidence.

The reflected waves returning to the probe, out of the waves irregularly reflected in the grain boundary of the material are received by the probe. The wave reception signal includes reflected waves from the first and the second layers having the different acoustic impedances in the depth direction. The reflection level of the ultrasonic waves in the MHz range in the layer having smaller grain particles is lower than that in the layer having larger grain particles. Accordingly, a boundary position where a difference in the reflection level is found is the boundary between the first and second layers. Thus, the distance between the surface of the material and the boundary is obtained by converting the time required for the ultrasonic waves to propagate this distance using the sonic velocity of the first layer.

The material is preferably a hardened material, and the first layer is a hard layer and the second layer is a layer of a base material. Then, the obtained measurement value is a thickness of the hard layer.

The sensor unit preferably comprises a local water immersion construction including a water reservoir having a water supply hole and an air-bubble discharge hole and having a surface which is in contact with the material and sealed by a transparent sealing tape; and a holder of a transparent material having a fixing hole above and in communication with the water reservoir into which the probe is inserted to be fixed.

In this apparatus, the probe is used after it is inserted into the fixing hole to be fixed and water is supplied to the water reservoir. Since the air-bubbles produced in the water reservoir during the supply of water are discharged through the air-bubble discharge hole, no air-bubble remains in the water reservoir. Further, since the water reservoir is transparent, the air-bubbles therein can be easily observed. Moreover, the contact surface with the material is sealed by the transparent sealing tape, and the space between the probe and the measurement surface of the material is filled with a propagation medium (water). Accordingly, the return loss during the propagation can be suppressed, and the ultrasonic waves having a specified level of energy is supplied to the material. Thus, this apparatus is effectively used in association with the local water immersion measuring method.

The apparatus advantageously comprises a water tank for containing water in which the material is immersed. The water tank is preferably provided with a mount for fixingly supporting the sensor unit with respect to the material immersed in the water.

Since the sensor unit is fixedly positioned by means of the mount with respect to the material immersed in the water tank, this apparatus is effectively used in association with the water immersion measuring method.

The mount is preferably capable of moving the sensor unit with respect to the surface of the material in the vertical direction. Then, the distance between the probe of the sensor unit and the surface of the material can be set at a suitable value.

The mount is preferably capable of moving the sensor unit at least in one axial direction in parallel with the surface of the material so that the sensor unit can scan the surface of the material. Then, the probe of the sensor unit can be positioned in a desired position on the surface of the material.

The probe is preferably formed by a piezoelectric device, and a matching coil for matching the impedance of the piezoelectric device and that of the extractor is preferably provided along a wave reception line between the piezoelectric device and the extractor.

In this apparatus, since the impedance of the piezoelectric device forming the probe and that of the extractor are matched by the matching coil, the signal representing the waves received by the piezoelectric device is input to the extractor at a maximum efficiency.

The extractor preferably integrates the wave reception signals obtained in association with a plurality of transmissions of the ultrasonic pulse, and detects the reflected waves from the boundary between the first and the second layers of the material to be measured based on the integrated wave reception signals.

In this apparatus, the reflected waves from the boundary between the first and the second layers of the material are detected by integrating the wave reception signal obtained in association with the plurality of transmissions of the ultrasonic pulse. Accordingly, a variation among the individual wave reception signals is eliminated, thereby providing a measurement result with a higher accuracy.

The extractor preferably includes a gate movable along a time axis and extracts, out of the wave reception signal, a first wave component which passes the gate as the reflected wave from the boundary between the first and second layers of the material to be measured.

In this apparatus, if the gate is provided along the depth direction extending from the measurement surface of the material, a high level wave reception signal representing the reflected waves from the measurement surface of the material is not mistakenly detected. Further, the level of the wave reception signal differs depending upon whether this signal represents the reflected waves from the first layer or the second layer of the material. In measuring the thickness of the hard layer, the reflection level of the first layer is lower because the grain particles are smaller, and that of the second layer is higher because the grain particles are larger. Accordingly, the first wave component passing the gate is extracted as the reflected wave from the boundary between the first and the second layers of the material.

The integrated wave reception signal is preferably averaged by the number of integrations. The apparatus may further comprise a display for displaying the waveform of the averaged wave reception signal.

In this apparatus, the wave reception signals obtained in association with the plurality of transmissions of the ultrasonic pulse; the integrated wave reception signal is averaged by being divided by the number of integrations (the number of wave transmissions/receptions); and the waveform of the averaged wave reception signal is displayed. Accordingly, a variation among the individual signals can be eliminated, and a S/N ratio when the reflected waves are indistinguishable from noises can be improved. Therefore, the highly accurate measurement result can be displayed, and the measurement result and the reflections in the first and the second layers can be confirmed.

These and other objects, features and advantages of the present invention will become more apparent upon a reading of the following detailed description and accompanying drawings.

BRIEF DESCRIPTION OF THE DRAWINGS

FIG. 11 is a sectional diagram showing a buildup of a stainless steel (SUS steel) welded on the surface of a carbon steel (SC steel);

FIG. 12 is a chart showing a waveform displayed on the cathode ray tube when a conventional ultrasonic measurement is performed to measure the thickness of the buildup of the stainless steel (SUS steel) formed on the carbon steel (SC steel);

FIG. 13 is a chart showing a waveform displayed on the cathode ray tube when an ultrasonic measurement is performed to measure the thickness of the buildup of the stainless steel (SUS steel) formed on the carbon steel (SC steel);

DETAILED DESCRIPTION OF THE PREFERRED EMBODIMENTS OF THE INVENTION

Figure 2:
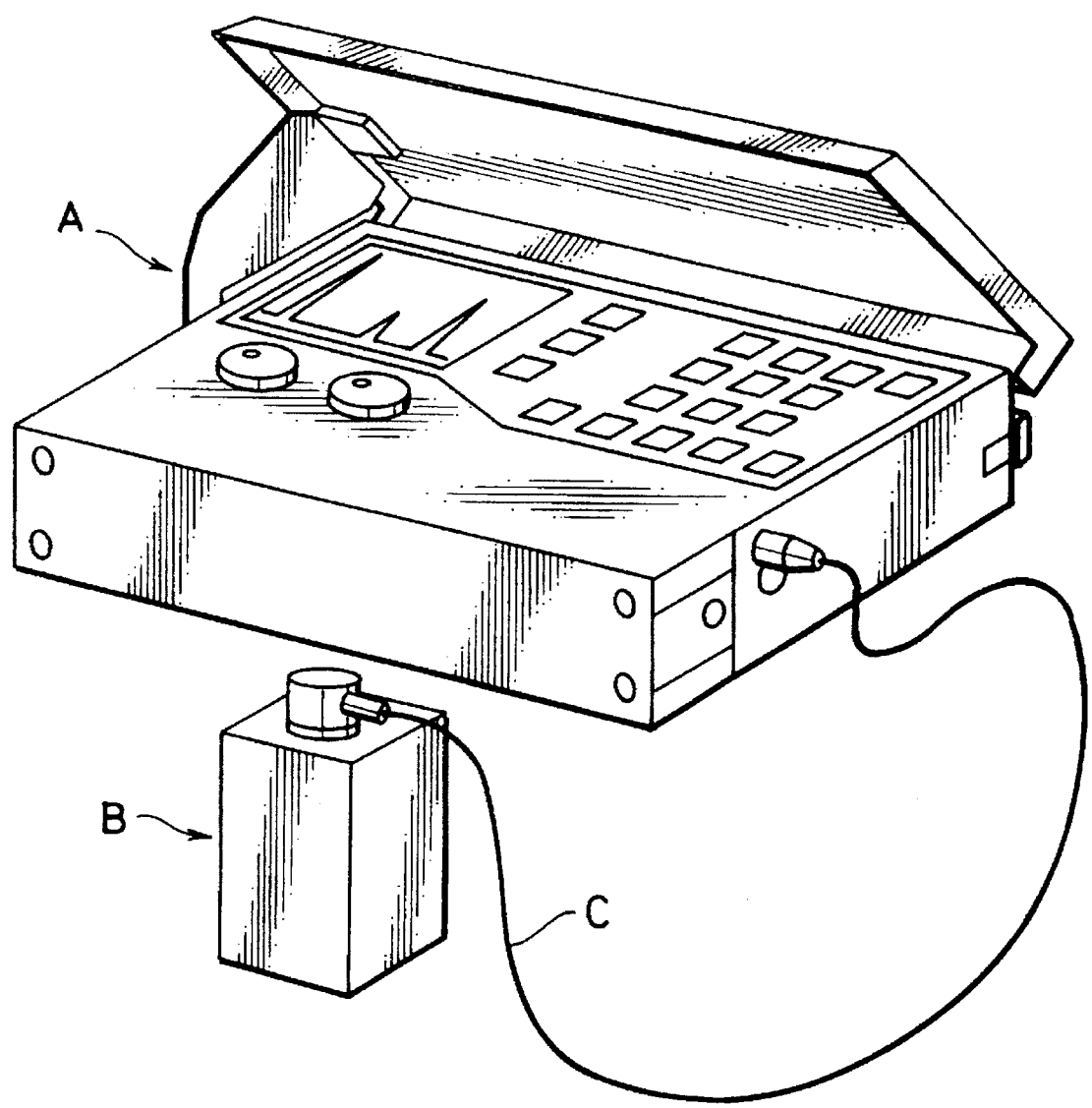
FIG. 2 is a perspective view showing an exterior of the layer thickness measuring apparatus.

FIG. 2 is a perspective view showing the exterior of an inventive layer thickness measuring apparatus using transverse waves of ultrasonic waves. This apparatus consists of a main unit A and a sensor unit B which are electrically connected by a cable C.

The main unit A is provided on its upper surface with an operation panel 40 used to instruct a variety of operations and a display 42. The main unit A is also provided internally with a variety of processors for generating an ultrasonic drive signal, applying specified signal processing to a wave reception signal representing a received wave and performing a calculation to measure a thickness of a hard layer and a thickness of a buildup of a material different from a base material. The sensor unit B is accommodated in a box-shaped housing, if necessary and is provided internally with a probe for transmitting and receiving ultrasonic waves and other various devices.

Figure 3:
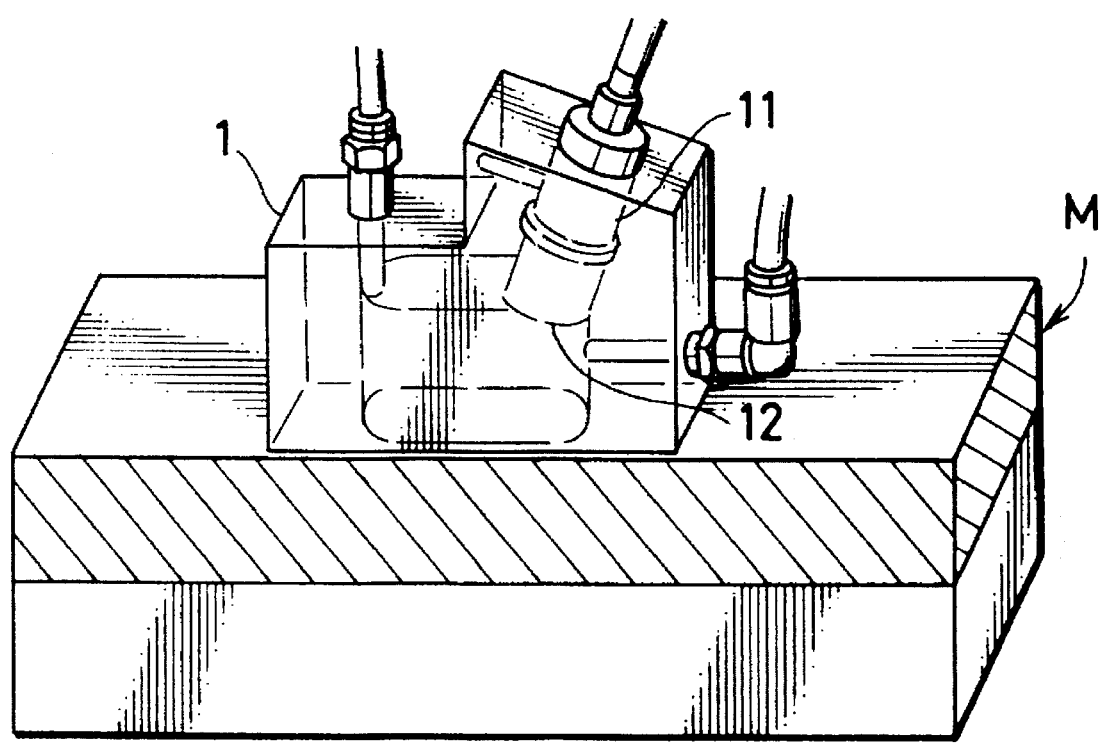
FIG. 3 is a perspective view showing how measurement is conducted by a probe mounted in a probe holder according to a local water immersion.
Figures 4A, 4B:
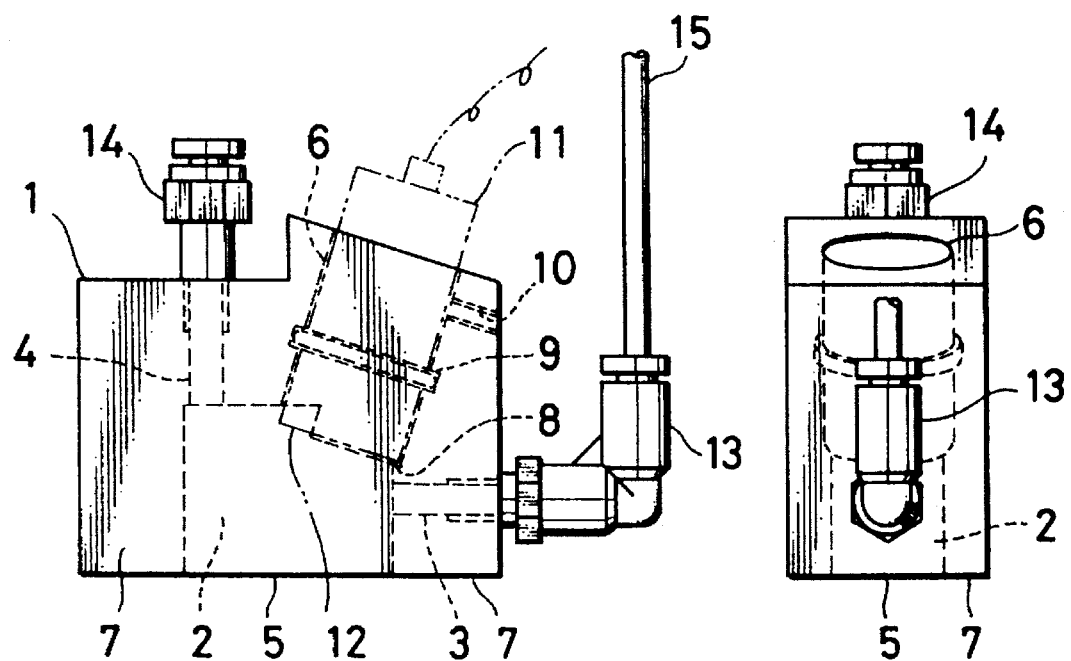
FIGS. 4A and 4B are a front view and a right side view of the probe mounted in the probe holder.
Figure 5:
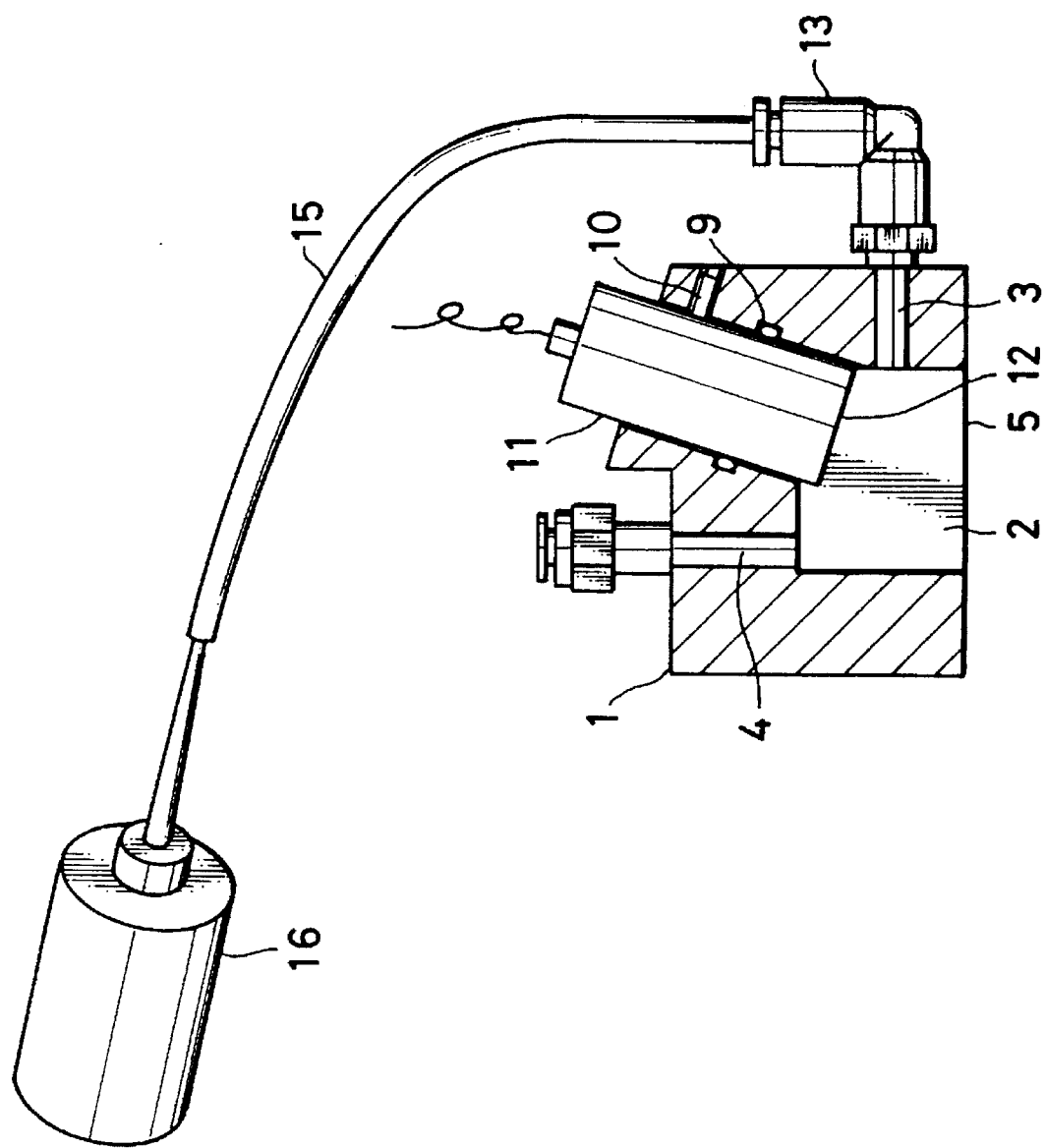
FIG. 5 is a side view partially in section of the probe holder showing how water is supplied.

The detailed construction of the sensor unit B is described with reference to FIGS. 3 to 5. FIG. 3 is a perspective view showing how a measurement is conducted by a probe mounted in a probe holder according to a local water immersion; FIGS. 4A and 4B are a front view and a right side view of the probe mounted in the probe holder; and FIG. 5 is a side view partially in section of the probe holder showing how water is supplied.

As shown in FIG. 3, the sensor unit B is disposed in contact with the upper surface of a material M to be measured. A measurement is performed with the sensor unit B in this position. The sensor unit B consists mainly of a probe 11 and a probe holder 11 for holding the probe 11 at a specified angle with respect to a vertical direction.

The probe 11 includes, for example, a quartz oscillator or a piezoelectric device of ceramic or other material. The probe 11 is excited by applying a high frequency drive voltage signal of 5 MHz or 10 MHz between electrodes formed on its opposite surfaces, thereby generating ultrasonic waves.

The probe holder 1 is substantially in the form of a parallelepiped and is made of a transparent acrylic resin. The probe 11 is mounted and fixed in a cylindrical fixing hole 6 (see FIG. 4) formed in a specified position on the upper surface of the probe holder 1. The probe holder 1 may also be made of a vinyl chloride resin, but the acrylic resin is preferable in terms of transparency and workability. With the probe 11 fixed in the fixing hole 6, ultrasonic waves are obliquely transmitted downward from a sensing surface 12, which is a wave transmitting surface formed at the lower end of the probe 11 (shown by dotted line in FIG. 4), and a reflected wave from the material M is received by the sensing surface 12. A diameter of the sensing surface 12 of the probe 11 is set at a suitable value in view of transmission energies and a suitable narrow directivity characteristic (angle of directivity). Though unillustrated, an acoustic ends may be opposed to the sensing surface 12 and a desired angle of directivity may be obtained by means of this acoustic lens. In the flaw detection, it is preferable to conduct a wide-angle examination. To the contrary, in the layer thickness measurement, it is necessary to eliminate unnecessary reflection noises as much as possible by transmitting ultrasonic waves on a spot.

As shown in FIG. 4, n the center of the probe holder 1, a water reservoir 2 formed with a recess having, for example, a rectangular or oblong circular horizontal cross-section extends from the bottom surface to the bottom end of the fixing hole 6, i.e., to a position where the sensing surface 12 is located. A water supply hole 3 and an air bubble discharge hole 4 communicate with the water reservoir 2 in positions different from the fixing hole 6.

The water supply hole 3 horizontally extends from one side surface of the probe holder 1 to an inner surface of the space forming the water reservoir 2. Water can be supplied into the water reservoir 2 from outside through a nozzle 13 including a water tube connector and the water supply hole 3. The air bubble discharge hole 4 extends vertically or substantially vertically from the upper surface of the probe holder 11 to the upper limit of the space forming the water reservoir 2. Air bubbles likely to be generated in water when the water is supplied into the water reservoir 2 are discharged through the discharge hole 4 and a nozzle 14 including a valve (not shown). Since the water supply hole 3 is disposed below the sensing surface 12 and the air bubble discharge hole 4 is disposed above the water reservoir 2, air bubbles generated during the supply of water can securely be discharged to the outside by the air remaining in the water reservoir 2.

A sealing tape S of polypropylene which is transparent and excellent in transmitting ultrasonic waves is adhered at the bottom surface of the water reservoir 2, i.e., a contact surface 7 with the material M to seal the interior of the water reservoir 2 so as to prevent a leak of water from the water reservoir 2. The dimensions of the water reservoir 2 are minimized to the extent that unnecessary virtual echoes are not generated. Accordingly, an area of the water reservoir 2 to be sealed by the sealing tape 5 can be made smaller to assure a sufficient sealing, and the probe holder 1 can be made smaller to have a better portability. Since the sealing tape 5 is abraded due to contact with the surface of the material during the measurement and thus needs to be frequently replaced, it is preferable to use an adhesive tape which can easily be replaced.

The fixing hole 6 in communication with the upper part of the water reservoir 2 is inclined with respect to the contact surface 7 in contact with the material M at an angle of 19° (angle of incidence). With the inclination of 19°, in the case where the material M is steel, an angle of refraction from water (in the water reservoir 2) to the steel becomes about 45° as indicated by dotted line in FIG. 4. This angle is preferable for efficient utilization of transverse waves (to assure suitable levels of propagated and reflected waves and to receive sufficiently strong waves). However, the angle of incidence is not limited to 19°, but may be any specified angle larger or smaller than 19° as long as the transverse waves can effectively be used.

In order to set the probe 11 at a specified distance in water, a stopper 8 is provided in the lower end of the fixing hole 6 using a part of the edge of the probe holder 1, and a seal ring 9 is provided in an intermediate part of the fixing hole 6. Further, in order to securely and stably fix the probe 11 in the fixing hole 6, a fixing screw 10 is spirally mounted in a hole extending from one side surface of the probe holder 1 at a right angle to the inner circumferential surface of the fixing hole 6.

When the probe 11 is to be set in the probe holder 1, the sealing tape 5 is first adhered on the contact surface 7 of the water reservoir 2 to seal the water reservoir 2. Next, the probe 11 is inserted into the fixing hole 6 to the stopper 8, and is fixed thereat by the fixing screw 10. In this state, the probe 11 is fixed at a specified distance in water. By providing the stopper 8 at the leading end of the fixing hole 6 a distance between the sensing surface (transmitting/receiving surface) 12 and the contact surface 7 in contact with the material M is always constant.

Subsequently, water is supplied to the water reservoir 2 of the probe holder 1. When supplying water to the water reservoir 2, the valve of the nozzle 14 is opened and water from, e.g. a pitcher 16 is supplied to the water reservoir 2 through a water supply tube 15 inserted into the nozzle 13 as shown in FIG. 5.

The transparent probe holder 1 has the following advantages. The inner wall of the water reservoir 2 and the sensing surface 12 can be carefully observed. The water can be supplied while adjusting the posture of the probe holder 1 to cause the water to flow along the sensing surface 12 so that bubbles do not remain on the inner wall of the water reservoir 2 and the sensing surface, and to cause the remaining bubbles to float and discharge through the discharge hole 4.

The supply of water is stopped when the water level reaches the discharge hole 4, and the valve of the nozzle 14 is closed. A leak of water between the fixing hole 6 of the probe holder 1 and the probe 11 is prevented by the seal ring 9 provided in the intermediate part of the fixing hole 6. Since the probe holder 1 is free from leaks of water and the holes 3 and 4 need not be plugged, the probe holder 1 can be easily carried around. Further, if the local water immersion is adopted, the measurement can be performed for a variety of shapes of materials. Particularly, this method is effective in measuring the thickness of the hard layer formed on the material having a large curvature, such as a gear and a cylindrical pipe. In this case, since the water reservoir 2 has a horizontal cross-section corresponding to the size of the sensing surface 12, even when the thickness of the hard layer is measured at a bottom surface between teeth of the gear, or the like, an accurate measurement can be performed by effectively blocking waves coming from portions near the position of measurement. If a probe holder 1 having a contact surface in conformity with the shape of a surface of the material M in the position of measurement is selectively used among probe holders having contact surfaces of different shapes, the probe 11 can be more stably held by the probe holder 1 and a measurement of a material having a curved surface is enabled by stabilizing a position and an angle of incidence of the ultrasonic waves. Although the sensor unit B is provided with the housing as shown in FIG. 2, the housing may not be necessary when the local water immersion is adopted.

Figure 6A:
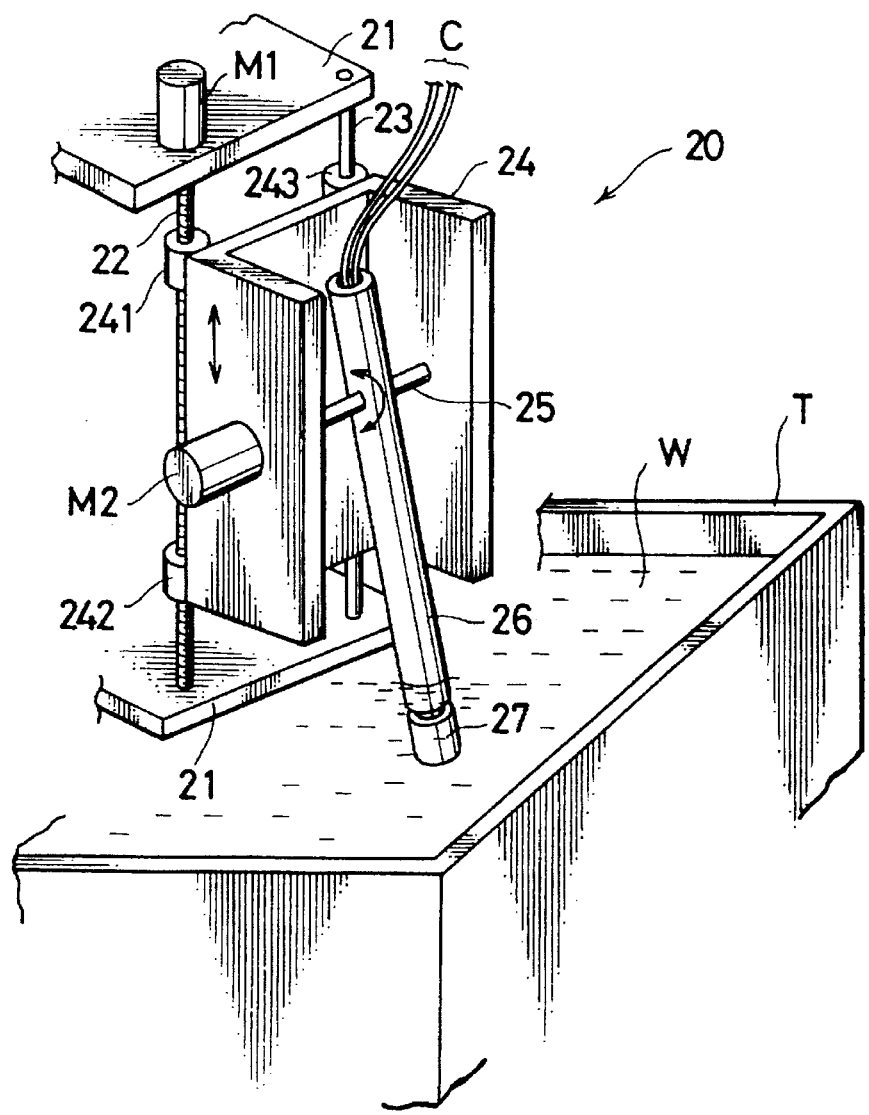
FIGS. 6A and 6B are perspective views showing a measuring apparatus used in association with the water immersion, FIG. 6A showing an elevating mechanism, and FIG. 6B showing a horizontal scanning mechanism.
Figure 6B:
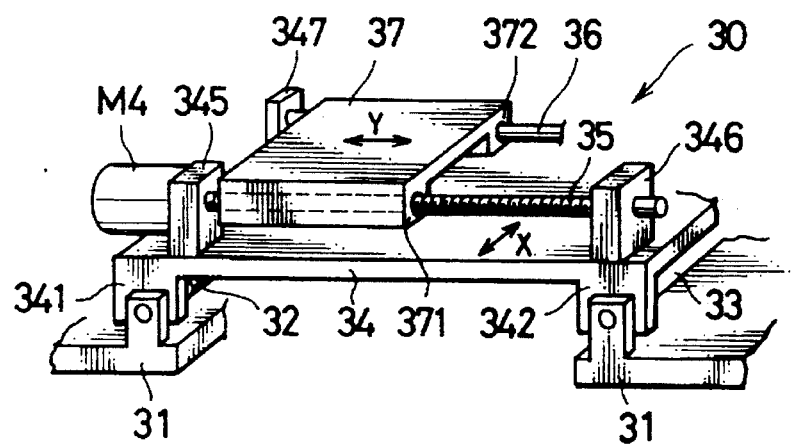

FIGS. 6A and 6B are perspective views showing an example of a measuring apparatus used in association with the water immersion, FIG. 6A showing an elevating mechanism and FIG. 6B showing a horizontal scanning mechanism.

A measuring apparatus used in association with the water immersion is provided with a water tank T for containing water in which the material M to be measured is immersed, and a mount mechanism for fixing or movably supporting the sensor unit B with respect to the material M immersed in the water tank T in a specified immersion position. The water tank T is, for example, in the form of a rectangular parallelepiped, and is filled with water W up to a specified level. Though unillustrated, a mount table for placing the material M immersed at a specified depth thereon such that a surface to be measured preferably extends in a horizontal direction. One or more materials M are placed side by side on the mount table.

In the elevating mechanism 20 shown in FIG. 6A, a pair of horizontal bases 21 are spaced apart in the vertical direction, and stays 22 and 23 are disposed in parallel relationship between the pair of the horizontal bases 21. The stay 22 is a ball screw rotatably supported by the horizontal bases 21. The upper end of the stay 22 is coupled with a rotatable shaft of a Z-axis motor M1. On the other hand, the stay 23 is a normal slide shaft. Indicated at 24 is a slidable member which is formed on its rear surface with engaging portions 241 to 244 engageable with the stays 22 and 23 (the engaging portion 244 is not shown in FIG. 6A). An internal thread is formed in the inner circumferential surface of each of the engaging portions 241 and 242 engageable with the stay 22. In this construction, when the Z-axis motor M1 is driven, the slidable member 24 is moved upward or downward according to a rotating direction of the Z-axis motor M1.

The slidable member 24 is formed such that it is U-shaped when viewed from above. A horizontal shaft 25 is mounted between the side walls of the slidable member 24. One end of the horizontal shaft 25 is coupled with a rotatable shaft of a θ-motor M2. A cylindrical rotatable member 26 is mounted in a substantially center position of the horizontal shaft 25, extending normal to the shaft 25. At the lower end of the rotatable member 26, there is mounted a watertight housing 27 for fixedly accommodating the probe 11. The housing 27 has a construction different from that of the housing of the measuring apparatus used in association with the local water immersion and shown in FIGS. 3 and 4: there is no construction for supplying and discharging water. At a lower end surface of the housing 27, the sensing surface 12 of the probe 11 is exposed directly or by way of an acoustic lens to directly transmit ultrasonic waves into water in the water tank T. Cables C are adapted to transmit an ultrasonic drive signal and a wave reception signal, and are connected with the main unit A by way of the cylindrical rotatable member 26.

The immersed material M is set at a specified distance by driving the Z-axis motor M1, and an angle at which the ultrasonic waves are incident upon the measurement surface of the material M is set at 19° or other desired value by driving the θ-motor M2. The distance adjustment by the Z-axis motor M1 enables measurements suitable for various materials M to be measured having layers of different thickness and particularly of different shapes such as different diameters.

In the horizontal scanning mechanism 30 shown in FIG. 6B, bases 31 are spaced apart by a specified distance. An ultrasonic measurement for the material M is performed between the bases 31. Stays 32 and 33 are mounted on the bases 31, extending in parallel with each other in an X-direction. One stay 32 is a ball screw, and one end thereof is coupled with a rotatable shaft of an X-axis motor M3 (not shown). The other stay 33 is a slide shaft. Indicated at 34 is an X-axis slidable member which is formed on its rear surface with engaging portions 341 to 344 engageable with the stays 32 and 33 (the engaging portion 342, 344 are not shown in FIG. 6B). An internal thread is formed in the inner circumferential surface of each of the engaging portions 341 and 342 engageable with the stay 32. In this construction, when the X-axis motor M3 is driven, the slidable member 34 is reciprocatingly moved along the X-axis direction according to a rotating direction of the X-axis motor M3.

At four corners of the upper surface of the slidable member 34, there are provided engaging portions 345 to 348 (the engaging portion 348 is not shown) each of which has an engaging hole extending in a direction normal to the X-axis. Stays 35 and 38 are mounted in parallel between the engaging holes 345 and 348 and between the engaging holes 347 and 348. The stay 35 is a ball screw, and one end thereof is coupled with a rotatable shaft of a Y-axis motor M4. The other stay 36 is a slide shaft. Indicated at 37 is a Y-axis slidable member which is formed on its opposite sides with respect to the X-axis direction with engaging portions 371 and 372 engageable with the stays 35 and 36. An internal thread is formed in the inner circumferential surface of each of the engaging portion 371 of the Y-axis slidable member. In this construction, when the Y-axis motor M4 is driven, the slidable member 37 is reciprocatingly moved along the Y-axis direction according to a rotating direction of the Y-axis motor M4.

The horizontal bases 21 can be reciprocatingly moved along both the X-axis and Y-axis direction by placing the bases 21 on the Y-axis slidable member 37, or placing the Y-axis slidable member 37 on the bases 21. Such a movement enables a predetermined scanning on the measurement surface of the material M.

With reference to FIGS. 8 to 13, there are described measurement results of the thickness of the hard layer and the measurement results of the thickness of the buildup of a different material formed on a base material by means of welding. Both measurement results are obtained by the measuring apparatus adopting the local water immersion method.

Hardened carbon steel S48C was used as a material M to be measured, and the thickness of the hard layer was measured in a macrostructure observation, a hardness test, and an ultrasonic measurement.

Figure 8:
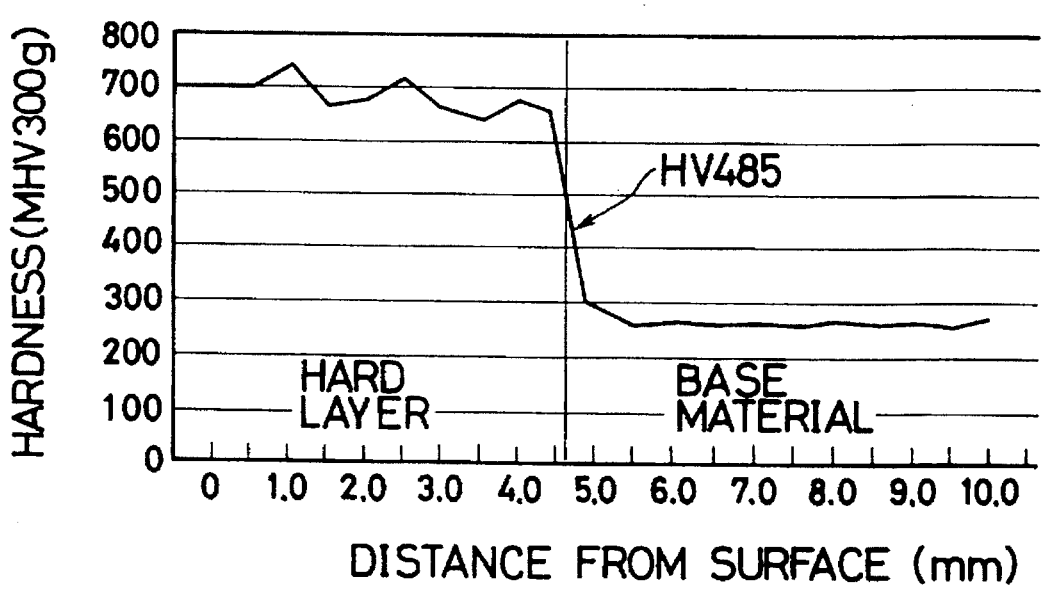
FIG. 8 is a graph showing a distribution of Vickers hardness of a hard layer of a specimen.

The thickness of the hard layer measured in the macrostructure observation was 4.7 mm. Thickness of the hard layer measured in the hardness test was 4.6 mm and the hardness at an effective depth was HV485 as shown in FIG. 8. The hardness test was a Vickers hardness test with a load of 300 g and a pitch of 0.5 mm.

Figure 9:
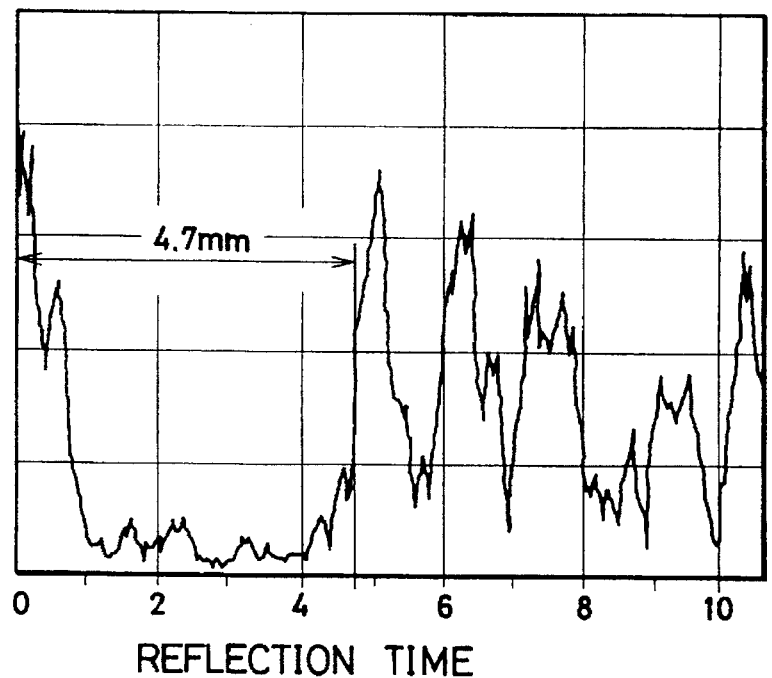
FIG. 9 is a chart showing a waveform displayed on a cathode ray tube when an ultrasonic measurement is performed to measure a thickness of a hard layer.

In the ultrasonic measurement by the inventive measuring apparatus, the thickness of the hard layer was 4.7 mm as shown in FIG. 9. The angle of incidence of the ultrasonic waves was 19°, and the angle of refraction thereof was 45°. As seen from the above measurement results, the thickness of the hard layer can be measured in the ultrasonic measurement as accurately as in the macrostructure observation and the hardness test.

In the measurement by the inventive measuring apparatus, the angle of refraction of the ultrasonic waves at the material M is 45°, i.e. is inclined by setting the angle of incidence thereof at, e.g. 19°. Accordingly, the transverse waves of the ultrasonic waves can be effectively utilized, and causes an irregular refraction at an intensity corresponding to the size of the grains in the grain boundary of the material M. Reflected waves which are a part of the irregularly refracted waves and propagate in a direction opposite from the transmitting direction of the ultrasonic waves are received by the probe 11. At this stage, because of the characteristic of the transverse waves, the ultrasonic waves transmitting into the steel material and transmitting from the interior of the steel material to the surface thereof are both at low level. As a result, energies of the transmitted waves are lost to only a small extent. Since a detection level of the reflected waves of the transverse waves in the steel material is not as remarkable as that of longitudinal waves (because of their large attenuance resulting from their short wavelengths), detected components are low level (this is taken care of by increasing a gain). However, since the sonic velocity of the transverse waves is about half as high as that of the longitudinal waves, the distance resolution, i.e., the detected distance accuracy thereof can be improved about twofold.

Before the hardening, the grain boundary in the steel material is substantially uniform or random. Accordingly, even if the transverse waves of the ultrasonic waves are caused to be incident upon the steel material in this state, the reflected waves from any depth position have substantially the same level or show no correlation. Such a steel material is heated and cooled. The size of the grains differs between the surface of the material which is rapidly cooled (hardened) (hard layer) and the interior thereof which is gradually cooled (base material). As a result, the greater the size of the crystal particles, the stronger the transverse waves of the ultrasonic waves having the same frequency are reflected. A reflection level becomes discontinuous at a boundary surface between the hard layer and the base material.

If the reflected waves are analyzed with reference to FIG. 9, the first reflected waves are those from the surface of the steel material, and the reflected waves from the hard layer follow thereafter during a period of low level. High level reflected waves drastically and randomly found are those coming from the interior of the base material. Particularly, the first high level reflected waves after the period of the low level correspond to the reflected waves from the boundary surface between the hard layer and the base material. Therefore, a time elapsing from the first reflected waves to the reflected waves from the boundary surface is converted into a distance using a known sonic velocity data. The converted distance is the thickness of the hard layer.

Figure 10:
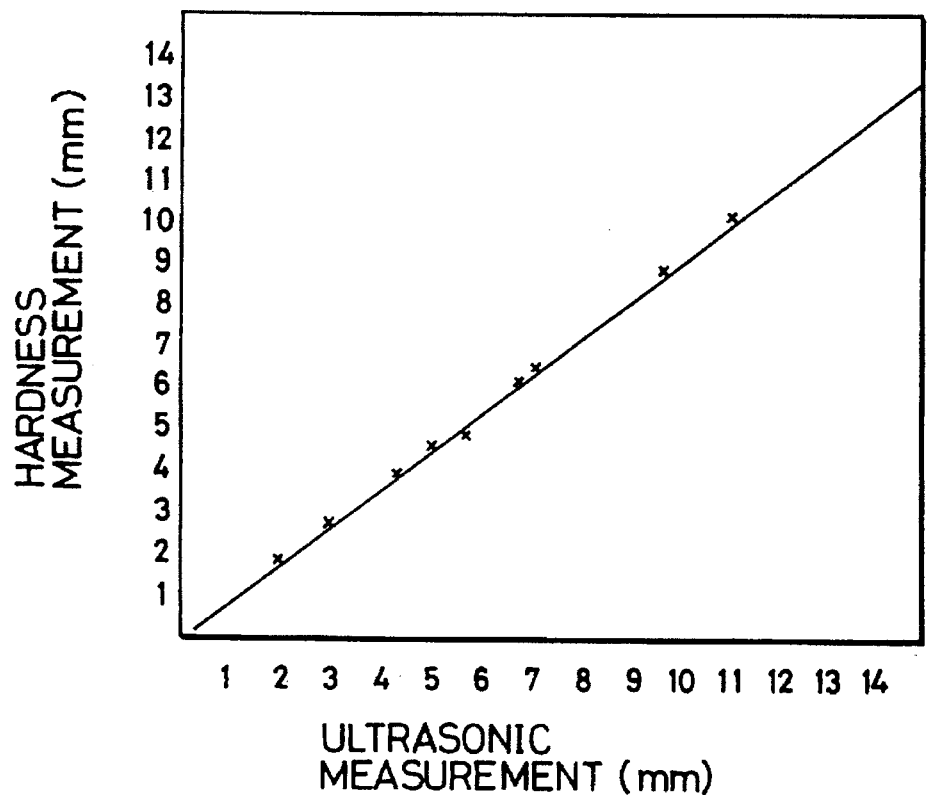
FIG. 10 is a graph showing a relationship between the thickness of a hard layer measured according to a hardness text and that obtained according to the ultrasonic measurement.

The relationship between the measurement values obtained in the hardness test and those obtained in the ultrasonic measurement for the measurement results other than the above is shown in FIG. 10, wherein X denotes the respective measurement values. As is clear from FIG. 10, the measurement values obtained in the hardness test and those obtained in the ultrasonic measurement substantially coincide, which shows that the inventive measuring apparatus is effective in measuring the thickness of the hard layer.

The measurement results for the thickness of the build-up of the different material at the welded portion is described with reference to FIG. 11. Stainless steel (SUS steel) was welded on the surface of carbon steel (SC steel) having a thickness of 300 mm to form a buildup, and the thickness of the thus formed buildup was measured. According to the conventional method adopting a vertical two separation direct contact method, since the attenuance of the ultrasonic waves in the stainless steel is large, the reflected waves from the boundary surface of the welded portion become indistinguishable. As a result, the thickness of the buildup cannot be measured. Further, if the ultrasonic waves are transmitted from the rear side, i.e., from the side of the carbon steel, the cathode ray tube needs to have a time axis of longer than 300 mm. This presents a problem in measuring the thickness of the thin buildup.

In the measurement by the inventive measuring apparatus, the ultrasonic waves are obliquely transmitted. Accordingly, the transverse waves of the ultrasonic waves are incident upon the material M. Because the transverse waves have a small attenuance at the surface of the steel material as described above, the measurement can be performed from the side of the SUS steel. Further, since the reflection level of the SUS steel is lower than that of the SC steel, the thickness of the buildup of the SUB steel can be measured using a difference between these levels. As a result of the ultrasonic test, the thickness of the buildup of the SUS steel was 4.3 mm. The angles of incidence and refraction of the ultrasonic waves in this test were 19° and 45°, respectively.

Next, the inventive apparatus is described with reference to a block diagram of FIG. 1.

The operation panel 40 includes dials 40a, 40b and operation keys 401 to 418 to be described later. The display 42 has a rectangular screen, and is formed by a liquid crystal display (LCD). The display 42 displays a waveform of the wave reception signal and the measurement data according to the operation of the operation keys in addition to a menu for a variety of instructions.

A controller formed by a microcomputer 43 changes the display contents and the set measurement conditions according to the operation of the dial 40a, 40b and the operation keys 401 to 418, processes the wave reception signal, and conducts a variety of calculations. For example, the controller 43 calculates an angle of refraction in a registration mode to be described later, compares a first intersection between a gate mark GM and the wave reception signal, and converts the measurement result, i.e. a time data into a distance data. Further, for these processings, the controller 43 sends timing signals and command signals used to centrally instruct and control the operation of the respective circuits provided in the main unit A. A software for these operations and controls is written in a program ROM 44. Indicated at 45 is a RAM for temporarily storing the processed data and the like, or storing them as storage data for a predetermined period of time (until a renewal or an erasure is instructed).

Figure 1:
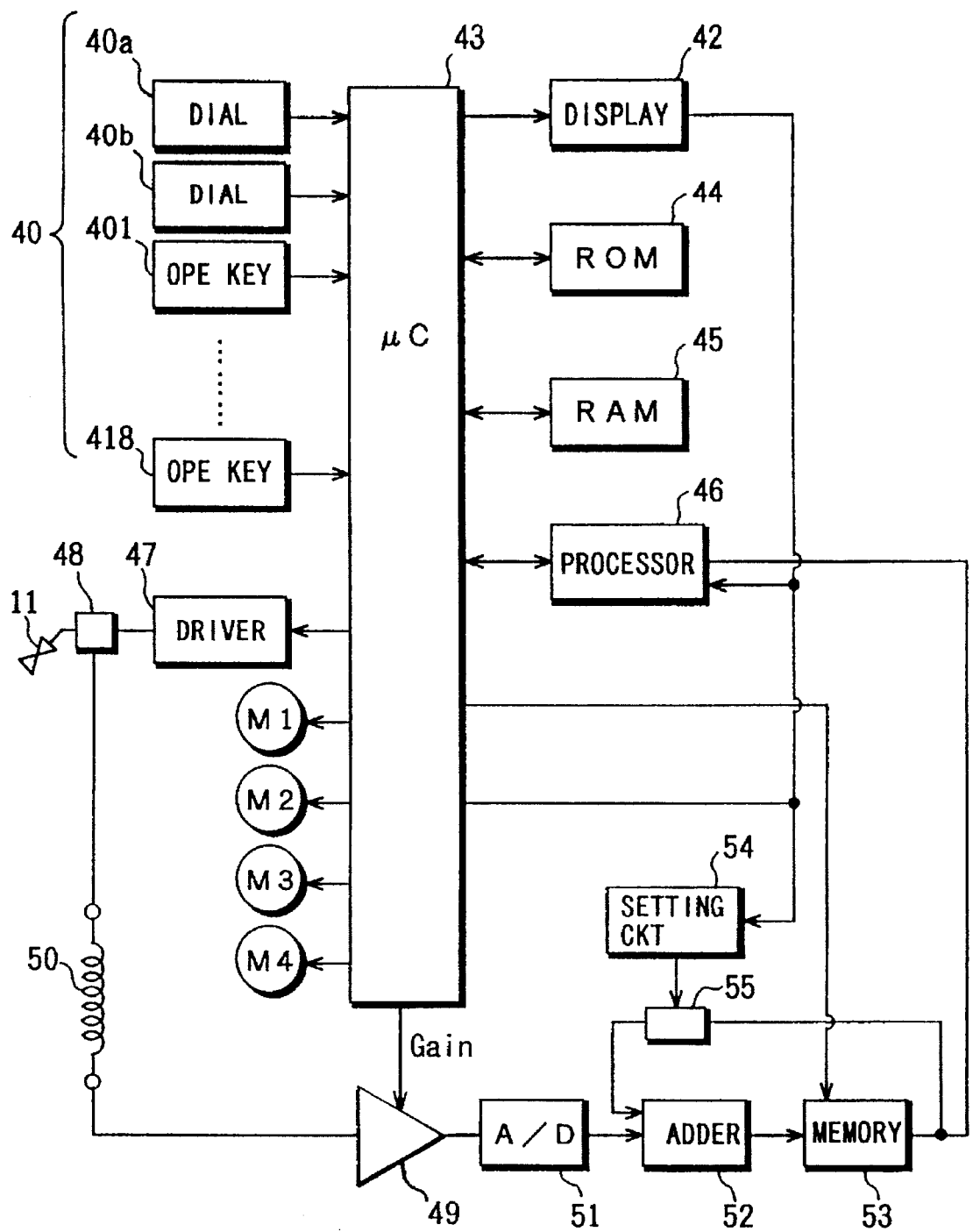
FIG. 1 is a block diagram showing an inventive layer thickness measuring apparatus using transverse waves of ultrasonic waves.

Though unillustrated in FIG. 1, a printer may be connected with the measuring apparatus so that the measurement data and the waveform of the wave reception signal can be output in the form of a hard copy, if necessary. Indicated at 46 is a processor for performing a variety of processings and calculations to be described later.

Indicated at 47 is a driver for generating a drive signal of a specified high frequency such as 5 MHz or 10 MHz which is used to transmit an ultrasonic pulse from the probe 11. The driver 47 sends a drive signal of a specified pulse duration upon each receipt of a cyclical transmission command signal from the controller 43. The drive signal is fed to the probe 11 by way of a transmission line and a transmission/reception switching circuit 48. On the other hand, after being received by the probe 11, the reflected waves from the material M are switched to a reception line by the switching circuit 48 and fed to an amplifier 49. The amplifier 49 is capable of amplifying the input high frequency wave reception signal to about 90 dB (decibels) which is in the vicinity of a limit of the amplifier 49. A gain of the amplifier 49 is controlled according to a level of a voltage applied to a gain control terminal. The limit of the amplifier 49 refers to a gain limit where the signal and the noise are distinguishable.

A matching coil 50 is provided along the reception line between the probe 11 and the amplifier 49 for matching the impedance of the probe 11 and that of the reception line, so that only the impedance of motors serves as a pure resistance downstream from the amplifier 49. This leads to an increase in a signal transmission efficiency, i.e., in a signal-to-noise (S/N) ratio.

This is explained with reference to an equivalent circuit diagram of FIG. 7.

The inventive measuring apparatus requires a gain of about 110 dB as a total sensitivity, but the gain limit of the amplifier 49 is about 90 dB as described above. Even if the gain is increased only by the amplifier 49, the impedance match cannot always be realized because noise components generated in a circuitry of the amplifier 49 become critical, because various materials are used to form the probe 11, and because the cable C is required to have a sufficient length to effectively use the sensor unit B. Accordingly, the noises and the wave reception signal gradually become indistinguishable, with the result that the impedance match relies on a difficult calculation. In view thereof, the S/N ratio is increased using the matching coil 50. i.e. the gain is assured to a required level, so that the impedance match can be realized by performed the calculation which is not excessive for the controller 43.

Figure 7:
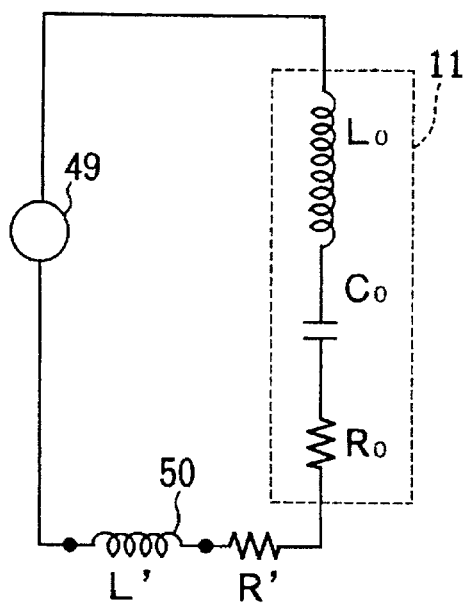
FIG. 7 is a diagram showing an equivalent circuit of a probe and a matching coil.

In FIG. 7, the impedance of the probe 11 can be expressed by a reacatance L0, a conductance C0, and a resistance R0. On the other hand, the matching coil 50 can be expressed by a reactance L', a sum R' of a resistance of the matching coil 50 and a resistance between the probe 11 and the amplifier 49 (cable C). In this case, the impedance Z of the circuit is expressed in the following equation:

$$Z=R+j(\omega L-1/\omega C0)$$

where

L=L0+L', R=R0+R', and ω=2πf.

In the above equation, when ωL−1/ωC=0, the impedance Z of the circuit becomes at minimum, i.e., is brought into a resonant state. Accordingly, in this state, the circuit can be used at the best sensitivity. For example, when a used frequency f is 10 MHz, a reactance L of the cable C (coaxial line)/1 m is 0.1 μh (microhenry), and the gain can be increased by about 20 dB. The matching coil 50 may be provided in the housing of the probe 11. Further, the matching coil 50 may have a variable reactance. In this case, the matching coil 50 can suitably respond to a change of a characteristic resulting from the deterioration of the probe 11 and a change in the length of the cable.

Referring back to FIG. 1, indicated at M1 to M4 are the Z-axis motor, the θ-axis motor, the X-axis motor, and the Y-axis motor, respectively.

Indicated at 51 is an analog-to-digital (A/D) converter for sampling the analog wave reception signal having passed through the amplifier 49 at a high speed and converting it into a digital wave reception signal, which is stored in a memory 53 via an adder circuit 52 in time series.

The adder circuit 52 adds the present digital wave reception signal and the one stored in the memory 53 with their time axes coincided. The memory 53 has a storage capacity corresponding to at least a product of a bit number in a level direction of the added digital wave reception signal and a sampling number.

Indicated at 54 is a setting circuit for setting the number of integrations in the level direction of the digital wave reception signal by the adder circuit 52. When the number of integrations becomes in excess of a set number, the setting circuit 54 sends a reset signal to open a gate 55, thereby preventing the digital wave reception signal from returning from the memory 53 to the adder circuit 52. The reset signal from the setting circuit 54 is also sent to the processor 46. In accordance with this reset signal, the specified calculation is applied to the wave reception signal and the calculation results are displayed.

The dials 40a, 40b and the operation keys 401 to 418 of the operation panel 40 are described with reference to FIGS. 2 and 14.

As shown in FIG. 2, the dials 40a, 40b rotatable in forward and reverse directions are provided at the left side of the main unit A.

The dial 40a is an X-axis/fine adjustment dial. The dial 40a is operated to scroll a display area along the X-axis (along the horizontal direction on the LCD screen, i.e. along the time axis) and to make a fine adjustment in setting the respective functions such as a measurement area and the sonic velocity.

The dial 40b is a Y-axis/rough adjustment dial. The dial 40b is operated to select the respective functions, to scroll the display along the Y-axis, and to make a rough adjustment in setting the respective functions. Both dials 40a and 40b are infinitely rotatable, and their amounts and directions of rotation are detected by encoders coupled with the respective dials.

Figure 14:
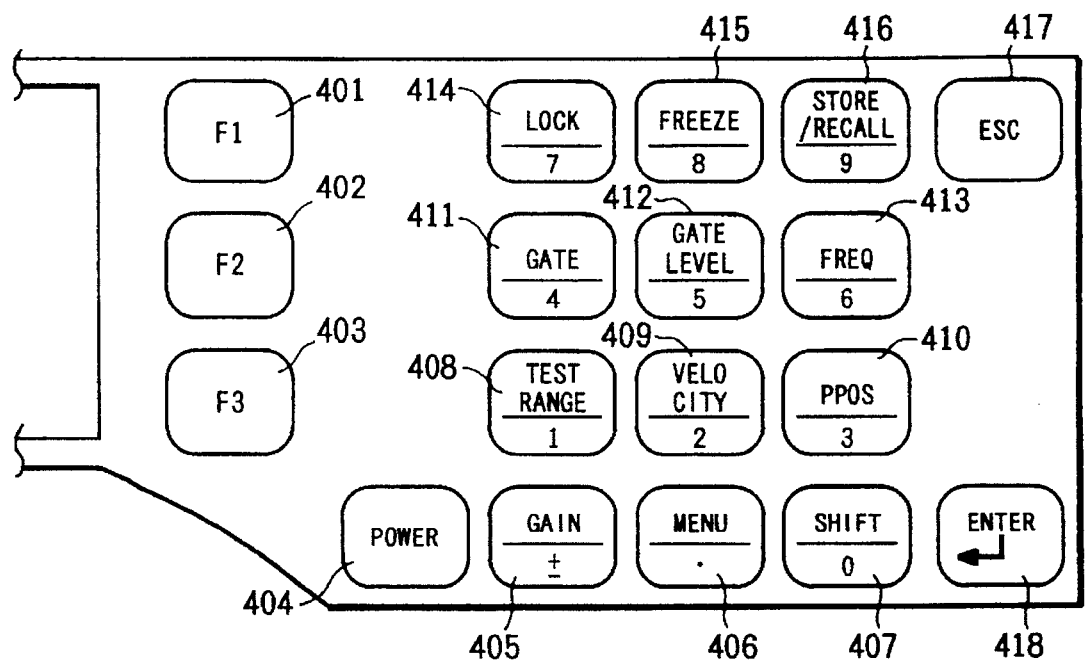
FIG. 14 is a plan view of a variety of operation keys provided in an operation panel.

F1 to F2 keys 401 to 403 are vertically arranged at the left end of FIG. 14.

The F1 key 401 is operated to instruct an initial screen display after the power is turned on. Further, every time the F1 key 401 is pressed, the stage-hike images are moved backward so that a previous image is displayed.

The F2 key 402 is operated to instruct a system operation and a display mode (AS non-display mode: measurement 1 operation) for displaying measurement data during the measurement. F2 key 402 is also used to adjust the height of the gate mark when it is pressed while a gate key 411 to be described later is pressed.

The F3 key 403 is operated to instruct the registration mode and a waveform display mode (AS display mode: measurement 2 operation) during the measurement. F3 key 403 is also used to adjust the range of the gate when it is pressed while the gate key 411 is pressed.

A power key 404 is operated to turn a power supply to the main unit A on and off.

A gain key 405 is operated to instruct a gain adjustment mode.

A menu key 406 is operate to instruct a display of a selection screen for selecting a function among a variety of accessory functions.

A shift key 407 is operated to perform a measurement from a point of incidence P0 on the time axis. When the shift key 407 is pressed, a data display frame for displaying the measured thickness data (see FIG. 16A) and the point P0 on the time axis is selected as a starting point of the thickness measurement. Further, this key 407 is pressed before inputting numerical values using ten keys, and is used to release a lock.

A measurement area key 408 is operated to instruct a measurement area adjustment mode. When this key 408 is pressed, a peak point of the reflected waves from the surface is selected as a starting point of the thickness measurement. The keys 408 and 407 are selectively operated but, normally, the shift key 407 is selected to perform the measurement.

A sonic velocity key 409 is operated to adjust the sonic velocity in conformity with the material M.

A pulse position key 410 is operated to instruct a waveform moving mode for moving the waveform of the wave reception signal along the time axis of the screen.

The gate key 411 is operated to instruct a gate setting mode for setting the position (starting point) of the gate or the width of the gate. The gate is adapted to securely detect the intended reflected waves by eliminating the influence of a reverberation generated after the wave transmission and by effectively eliminating the reflected waves from the sealing tape 5 and the measurement surface of the material M and further the propagation distance in the water reservoir 2.

A monitor level key 412 is operated to instruct a monitor level setting mode for setting monitor levels (a warning level, a threshold value of a cross-section display) within a gate marker.

A test frequency key 413 is operated to instruct a frequency in a test measurement performed before a main measurement.

A lock key 414 is operated to temporarily invalidate or release the operations of all other keys. This key 414 effectively prevents an inadvertent key operation.

A freeze key 415 is adapted to temporarily make a stationary display of a waveform of the wave reception signal.

A store/read key 416 is operated to instruct a store/read mode for storing and reading the measurement conditions and the displayed waveform.

When an ESC key 417 is pressed once while a set screen image is displayed, the waveform of the wave reception signal is displayed.

An ENTER key 418 is operated to decide a selection item while the menu is displayed. The key 418 is also used to instruct a printout of the screen image showing the thickness of the hard layer (see FIG. 16A) and the screen image showing the stored measurement values (see FIG. 16B) which images are made stationary by pressing the freeze key 415.

After the shift key 407 is pressed, the keys 407 to 416 may be used as ten keys to input numerical values.

Figure 15:
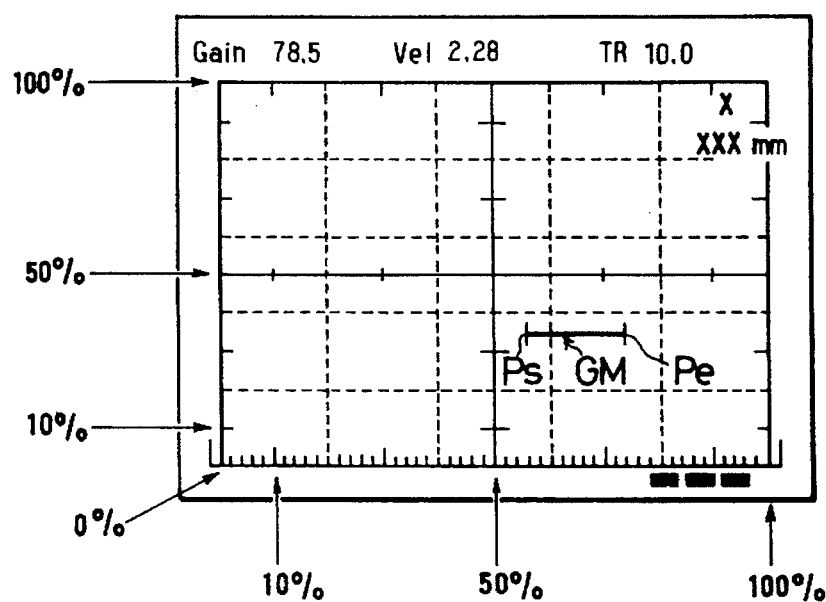
FIG. 15 is a diagram showing an exemplary layout on a screen of a display unit displaying a waveform of a received wave in an AS display mode.

Next, there is described a layout of a screen in the AS display mode for displaying the waveform of the wave reception signal in the display 42 with reference to FIG. 15.

A frame for displaying the waveform of the wave reception signal is displayed on the screen. Within this frame, dotted lines corresponding to 20%, 40%, 80%. 80% levels are displayed in parallel with the time axis (X-axis) and the level direction (Y-axis). Gauges of 2% are displayed along the time axis in order to make it easier to visually read the data and to set the gate marker GM. Solid lines representing 50% level intersect at right angles so that a center position of the frame can easily be seen.

The gate marker GM is in the form of a line segment extending along the time axis, and is displayed by setting its starting point Ps and its end point Pe by operating the F3 key 403 while pressing the gate key 411. The gate marker GM is movable in the level direction by operating the F2 key 402 while pressing the monitor level key 412. By operating these keys in the above manner, a gate area for extracting the waveform of the wave reception signal can be set at desired time and level.

Figures 16A, 16B:
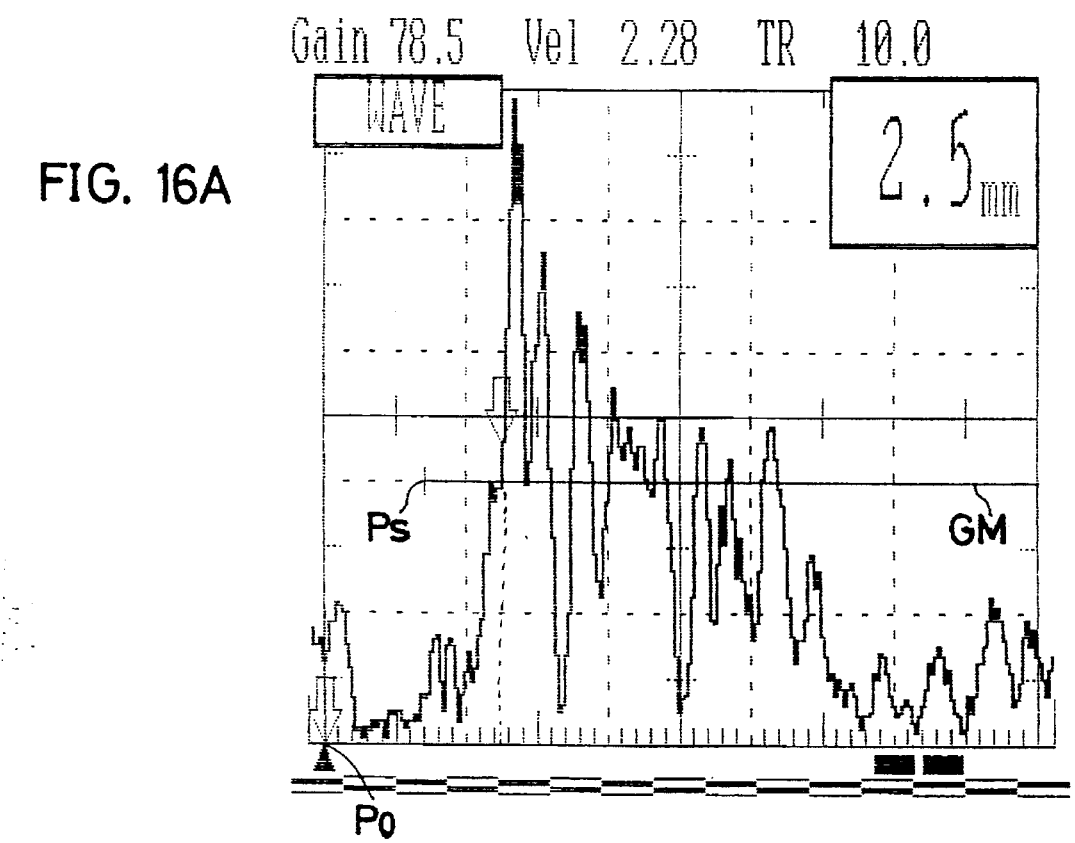
FIGS. 16A and 16B are diagrams showing displays made on the screen during the measurement, FIG. 16A showing a display in the AS display mode, and FIG. 16B showing a display in a non-AS display mode.

At an upper right corner of the frame, a duration which lasts from the point of incidence P0 until the wave reception signal first crosses the gate (indicated by an arrow in FIG. 16A) is converted into a length (mm) and displayed. During the actual measurement, a numerical value is displayed in large size within a frame at the upper right corner as shown in FIG. 16A. The peak value of the wave reception signal within the gate may be displayed in %. The point of incidence P0 is an origin of the display range of the time axis of the wave reception signal provided at the bottom of the frame, and is indicated by ▲.

The inventive measuring apparatus is operable with an internal battery as well as with a commercial power supply. In this case, a state of the battery (amount of remaining charges) is displayed in three stages at a lower right corner of the screen. This display is adapted to attract an attention, particularly, of an operator since the transmission level of the ultrasonic pulse influences a measurement accuracy. At the top of the screen, there are displayed from the left side a present gain, a present sonic velocity, and a present measurement area in numerical values, respectively. For example, 78.5 refers to 78.5 dB; 2.28 refers to 2.28 km/s (an average sonic velocity in the water reservoir 2 and the material); and 10.0 refers to 10.0 mm (a duration along the time axis converted into a length (mm)). The use of the internal battery is particularly preferable in terms of operability and portability in the case of the measuring apparatus adopting the local water immersion method as shown in FIG. 2. However, in the case of the measuring device adopting the water immersion method as shown in FIG. 6, the commercial power supply is used, considering an application of a drive power to a plurality of motors M1 to M4, etc.

FIGS. 16A and 16B are diagrams showing display contents on the screen during the measurement, FIG. 16A showing the display contents when the AS display mode is on and FIG. 16B showing the display contents when the AS display mode is off.

The waveform shown in FIG. 16A is not an analog wave reception signal, but a digital analog wave reception signal. In other words, the wave reception signals continuously obtained and integrated for the set number of times, i.e. 10 times are stored in the memory 55. The integrated signal is introduced to the processor 46 to be averaged in the level direction, and thereafter the averaged signal is displayed. Only the starting point Ps of the gate marker GM is set along the time axis, and the gate marker GM is about 1.5 mm. Further, the gate marker GM is set at about 40% in the level direction. A measurement value 2.5 mm displayed at the upper left corner of the screen is converted from a duration which lasts from the starting point to the first crossing of the wave reception signal and the gate marker GM along the time axis. The processor 46 searches the respective sampling levels of the waveform of the averaged wave reception signal in the time axis direction, compares the sampling levels with the set level of the gate marker GM, and calculates a distance from a sampling time data of the sampling signal which first coincides with the level of the gate marker GM and which is obtained by counting the number of sampling signals whose interval is set in advance. If the gate marker GM is not set, after accurately transmitting the reflected waves from the measurement surface of the material M at the point of incidence P0, a distance to the first high level reflected waves (e.g., a rise or middle portion of the waves) thereafter may be visually read using the gauges on the screen.

If the measurement is performed in real-time for the individual wave reception signals, it may not be accurately performed because of the possibility that the waveforms of the wave reception signals slightly differ depending upon even a slight change in the wave transmission conditions and a contact with the material M. Thus, such a measurement may require a skill or may be hindered. As in the invention, if the waveforms of a specified number of wave reception signal are averaged to find a correlation of a sufficient level and the measurement is performed based on the averaged waveform, i.e., the waveform having a correlation, highly stable and highly accurate measurement values can be obtained. Even in the case where the measurement values are visually read, they can be easily and accurately read. Further, since the reflective state in the hard layer and in the base material, and similarly the reflective state from the respective layers of the buildups of different materials can be stably confirmed, such confirmed contents can be utilized as one factor in deciding as to whether the steel itself is good or bad.

The waveform shown in FIG. 16 is not a geometric representation of the wave reception signal, but measurement values. For example, a numerical value. 2.5 mm in FIG. 16A is displayed. Within the screen, 50 measurement values (10 in column and 5 in row) can be displayed as a history data. More specifically, measurement values are displayed in the column direction from a position determined by the first column and the first row. Upon finishing one column, the display moves on to the next column. In the state shown in FIG. 16B, the 22nd measurement result is presently displayed. 0.0 or nothing is displayed in each position after the position corresponding to the 22nd measurement result since measurements have not yet been performed. Since 50 measurement values are at maximum obtainable for a single measurement position, for 50 different positions of a single material M, or for 50 materials M of the same kind, it is easy to accurately compare these values and, based on the comparison result, make a determination as to whether the material(s) M is/are good or bad.

Figure 18:
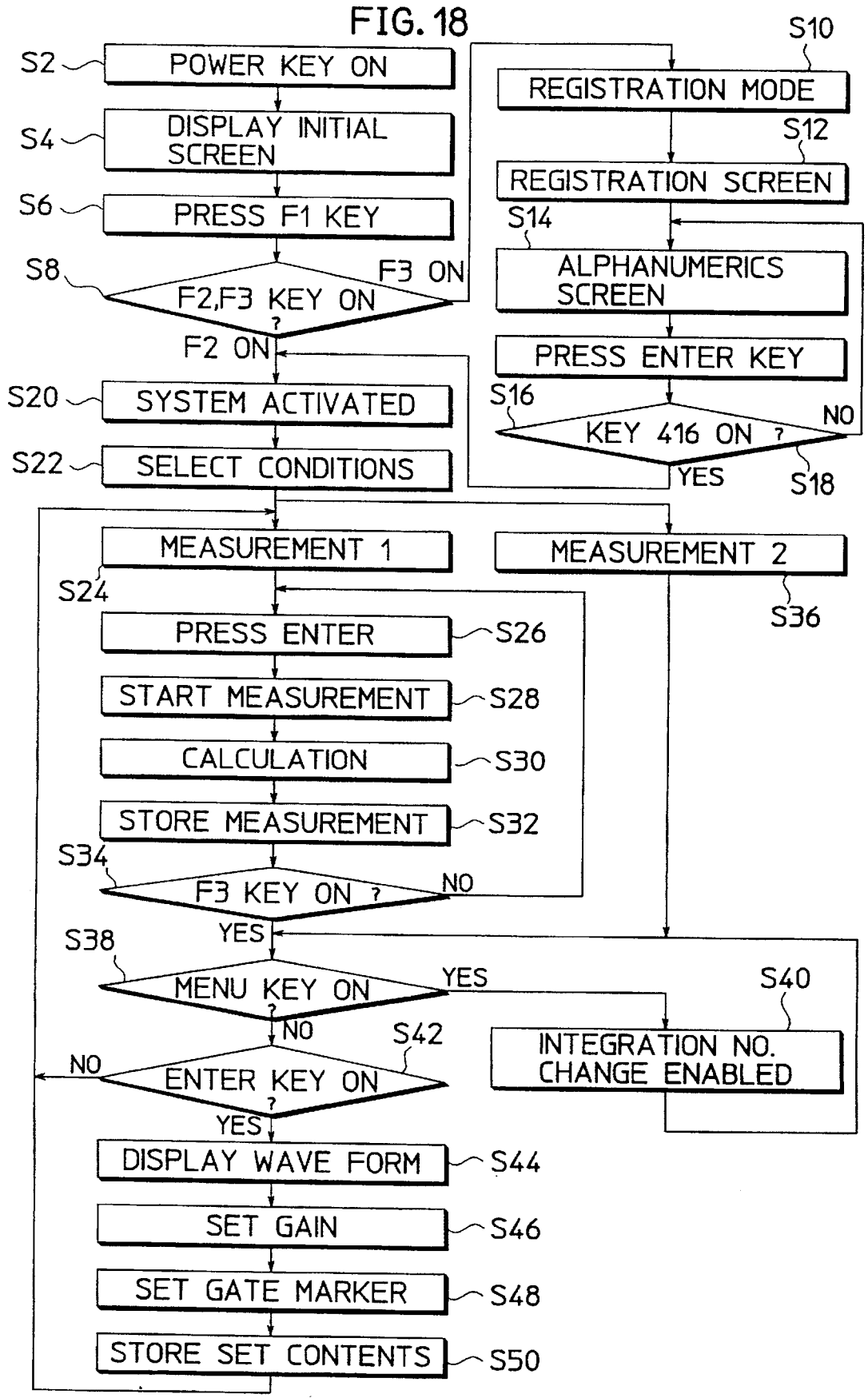
FIG. 18 is a flowchart schematically showing setting of measurement conditions and a measurement.

FIG. 18 is a flowchart schematically showing the setting of the measurement conditions and the measurement.

This flowchart is started when the power key 404 is operated (Step S2). When the power supply is turned on, the initial screen image is displayed on the display 42 (Step S4). On the initial screen, there are displayed, for example, the name of the apparatus, the name of the manufacturer, and the like. When the F1 key is pressed in this state (Step S6), a screen image corresponding to the AS display mode (FIG. 15) is displayed. At this stage, if the transmission of the ultrasonic waves from the probe 11 has been already started, the wave reception signal is displayed on the screen without the measurement conditions. The waveform of the signal being displayed is used as a standard for setting the measurement conditions.

In this state, it is discriminated which one of the F2 key 402 and the F3 403 key has been pressed (Step S8). If the F2 key 402 has been pressed, this routine proceeds to Step S20 in which the system is activated. If the F3 key 403 has been pressed, this routine enters a registration mode where the measurement conditions are set using basic functions (Step S10). It should be noted that, in the following operation steps, every time the F1 key 401 is pressed, the display returns to the screen image at the first stage is displayed.

In the registration mode, the setting of the measurement conditions is enabled. The setting of the measurement conditions includes a timing adjustment for the point of incidence shown in FIG. 15; the input of the angle of refraction; the setting of the duration, the gain, the gate marker GM and any desired condition. It should be appreciated that the angle of refraction is calculated by the processor 46 based on an acoustic impedance ratio of water to the material M and the angle of incidence.

The timing adjustment for the point of incidence P0 is made after the corresponding mode is set by pressing the pulse position key 410. Then, by rotating the dial 40a (fine adjustment) and/or the dial 40b (rough adjustment) to scroll the display time area accordingly (i.e. according to the amount and direction of rotation of the dials 40a and 40b).

Since the angle of refraction is a numerical value, after the shift key 407 is pressed to set a ten keys input mode, this value, e.g., "1", "9" (=19) is input using the ten keys.

The duration is set after the corresponding mode is set by pressing the measurement area key 408. Then, by rotating the dial 40a (fine adjustment) and/or the dial 40b (rough adjustment), the time axis is shortened or lengthened using the point of incidence PO as a reference according to the amount and direction of rotation of the dials 40a and 40b.

The gain adjustment is made by rotating the dial 40b after setting the gain adjustment mode by pressing the gain key 405. The gain value is obtained by converting the present amount and direction of the dial 40b in relation to the value set before the operation. The obtained gain value is displayed as a numerical value on the screen in the AS display mode, and is input to a gain adjustment terminal of the amplifier 49 in the form of a voltage signal.

The gate marker GM is set after setting the corresponding mode by pressing the gate key 411. Specifically, the starting Point Ps of the gate marker GM along the time axis is set by the dial 40a; the width thereof is set by the F3 key 403 (corresponding to the setting of the end point Pe); and the level is set by the F2 key 402.

Further, the sonic velocity, the number of integrations to be made, etc. can be set as accessory functions using the MENU key 406. The sonic velocity is determined based on the material M or the material of the buildup, and the determined value may be simply input.

Figure 17:
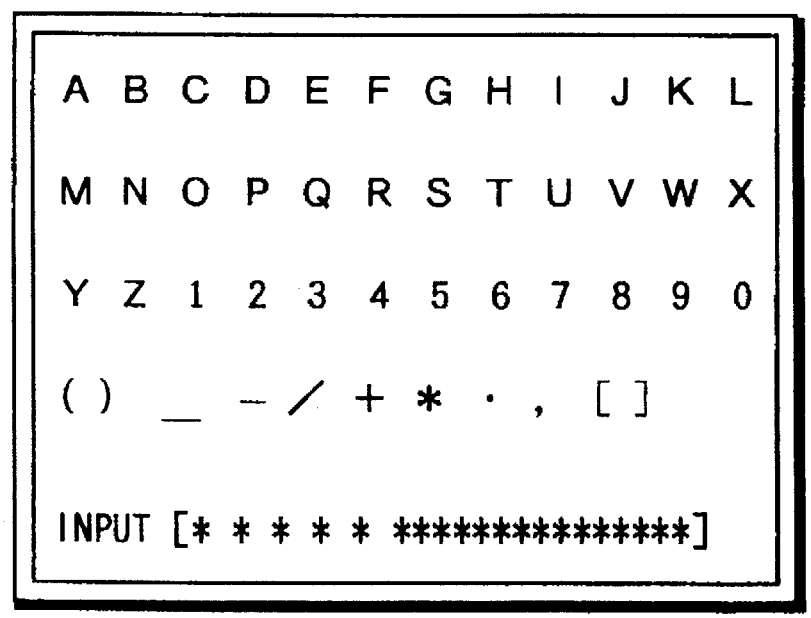
FIG. 17 is a diagram showing a screen of a display unit displaying alphanumerics.

Upon the completion of the setting of the measurement conditions, the F3 key 403 is pressed, and the screen image is switched to the one corresponding to the registration mode to conduct the registration of the set conditions (Step S12). In this screen image, a list of names of items registered in the past is displayed. When one of the registration items is to be renewed, a position designation marker is moved to a position where the corresponding registration item is displayed by means of the dial 40a, a new condition is written under this registration name, and the ENTER key 418 is pressed to complete the registration. A new registration name can be made as follows. When the F2 key 402 is pressed, the screen image including alphanumerics shown in FIG. 17 is displayed (Step S14). The desired letters are designated one after another by moving the position designation marker to the position of the letter using the dials 40a, 40b and pressing the ENTER key 418 (Step S16). It is then discriminated whether the store/read key 416 has been pressed (Step S18). If the key 416 has been pressed, it is assumed that the designation of the letters for the registration name has been completed, and a presently input content is written in the RAM 45 in correspondence with a new registration name. Then, this routine proceeds to Step S20. If the key 416 has not yet been pressed, it is assumed that the designation of the alphanumerics for the registration name has not yet been completed, and the next letter of the registration name is designated after pressing the F2 key 402 (a loop of Steps S14 to S18). Thereafter, the store/read key 416 is pressed.

In Step S20, the system for the measurement is activated, and the list of registration items is displayed so that the operator can select the measurement conditions (Step S22). The measurement conditions are selected as follows. The registration names corresponding to the desired measurement conditions including those set in the past and newly set for the present measurement are designated by means of the dial 40a. At this stage, if the F2 key 402 is pressed, this routine enters a measurement 1 mode under the designated measurement conditions without making the AF display (see FIG. 16B) (Step S24). On the other hand, if the F3 key 403 is pressed, this routine enters a measurement 2 mode under the designated measurement conditions while making the AF display (see FIG. 16A) (Step S36).

When the ENTER key 418 is pressed in the measurement 1 mode (Step S26), the ultrasonic waves are transmitted to start the measurement (Step S28). After the ultrasonic waves are repeatedly transmitted in a specified cycle by the set number of integrations, the obtained integration data (wave reception signals) are averaged, and the thickness of the hard layer is calculated from the average wave reception signal in relation to the gate marker GM as described above (Step S30). The obtained measurement value is stored in the RAM 45 (Step S32). Subsequently, it is discriminated whether the F3 key has been pressed, while proceeding to Step S26 unless otherwise. Each time the ENTER key 418 is pressed, the transmission of the ultrasonic waves by the number of integrations, and the calculation and storage of the measurement value are repeated (a loop of Steps S26 to S34).

In Step S38, it is discriminated whether the MENU key 406 has been pressed, the change of the number of integrations is enabled and the presently set value is changed according to the amount and direction of rotation of the dial 40a (Step S40). After the change is made or if the change is not to be made, it is discriminated whether the ENTER key 418 has been pressed (Step S42). If the key 418 has not yet been pressed, this routine returns to Step S24. If the key 418 has been pressed, a screen image with the signal waveform as shown in FIG. 16A is displayed (Step S44); the gain is set (or changed) (Step S46); and the starting point Ps of the gate marker GM is set (or changed) (Step S48). This routine skips these steps if no adjustment is necessary. When the gain and/or the starting point Ps of the gate marker GM are set (or changed), the newly set contents are stored in the RAM 45 in correspondence with the registration name (Step S50). Thereafter, this routine returns to Step S24.

Although the frequencies of the ultrasonic waves used in the foregoing embodiment are 5 MHz and 10 MHz, the invention is not limited to these frequencies. The similar effects are obtainable by using ultrasonic pulses lying in a, so-called, MHz range of about 1 MHz to several 10 MHz.

Further, according to the foregoing embodiment, the thickness of the hard layer (measurement value) is obtained based on a time which lapses until the first intersection with the waveform of the wave reception signal in the gate marker GM. However, the invention is not limited to the above. For example, a time required to reach, e.g. the half of the level where a first peak of the waveform is found within the gate marker GM may be obtained as a measurement value. Alternatively, a level different before and after a sampling level are successively obtained, and a time when this difference first becomes beyond a set threshold value in a negative direction may be obtained as a measurement value. If the detection level is set independently of the set level of the gate marker GM, the measurement value can be automatically obtained even when the gate is not set.

The invention can also be applied to measure the thickness of a layer formed on the surface by means of plating, metal spraying, covering, etc. in addition to the thickness of a hard layer and the thickness of a buildup of a different material.

According to the present invention, there are provided a sensor unit including a probe for obliquely transmitting and receiving to and from the surface of a material to be measured having first and second layers with different acoustic impedances in a depth direction, extractor for extracting, from a wave reception signal representing waves received by the probe, reflected waves from a boundary between the first and the second layers of the material, and calculator for calculating a distance between the surface of the material and the boundary. Accordingly, the distance can be measured between the surface of the material and a boundary between the first and the second layers having the different acoustic impedances in the depth direction.

This inventive apparatus can be applied for measurement of a thickness of a hard layer.

This inventive apparatus is advantageous in transportation, and able to remove air-bubble on the probe and in the medium, thereby assuring accurate measurement. A measuring apparatus of the present which adopts a local water immersion measuring method enables measurement of a thickness of a thin hardened layer, and can eliminate a large water tank equipment. Also, the inventive apparatus can be freely moved. Accordingly, thickness measurement can be accurately carried out without moving materials to be measured.

The water tank is provided with a mount for fixingly supporting the sensor unit with respect to the material immersed in the water. Accordingly, this apparatus can be effectively used in association with the water immersion measuring method.

The mount is capable of moving the sensor unit with respect to the surface of the material in the vertical direction. Accordingly, this apparatus can be effectively used for a variety of materials having different layer thicknesses, different sizes, or different shapes.

Also, the mount is capable of moving the sensor unit at least in one axial direction in parallel with the surface of the material. The probe of the sensor unit can be positioned in a desired position on the surface of the material.

The impedance of the piezoelectric device forming the probe and that of the extractor are matched by the matching coil. Accordingly, the signal representing the waves received by the piezoelectric device is input to the extractor at only a resistance reduction or at a maximum efficiency.

The extractor integrates the wave reception signals obtained in association with a plurality of transmissions of the ultrasonic pulse, and detects the reflected waves from the boundary between the first and the second layers of the material to be measured based on the integrated wave reception signals. Accordingly, a variation among the individual wave reception signals is eliminated, thereby providing a measurement result with a higher accuracy.

The extractor includes a gate movable along a time axis and extracts, out of the wave reception signal, a first wave component which passes the gate as the reflected wave from the boundary between the first and second layers of the material to be measured. Accordingly, a reflected wave from the boundary between the first and second layers can be received more assuredly, thereby providing a higher reliability.

The integrated wave reception signal is averaged by the number of integrations. There is further provided a display for displaying the waveform of the averaged wave reception signal. Accordingly, a variation among the individual signals is eliminated to provide a highly accurately measurement result which is in turn displayed. Also, the reflections in the first and the second layers can be confirmed.

What is claimed is:

1. An apparatus for measuring a thickness of a layer, comprising:

a sensor unit including a probe for obliquely transmitting and receiving waves to and from the surface of a material to be measured having first and second layers with different grain sizes of grain particles in a depth direction;

an extractor for extracting, from a wave reception signal representing waves received by the probe, signals of waves that are reflected by the grain particles of the material; and a calculator for calculating a distance between the surface of the material and a change in the grain sizes of the grain particles from said signals of waves.

2. An apparatus according to claim 1, wherein the material is a hardened material and the first layer is a hard layer and the second layer is a layer of a base material.

3. An apparatus according to claim 1, wherein the sensor unit comprises a local water immersion construction including:

a water reservoir having a water supply hole and an air-bubble discharge hole and having a surface which is in contact with the material and sealed by a transparent sealing tape; and a holder of a transparent material having a fixing hole above and in communication with the water reservoir into which the probe is inserted to be fixed.

4. An apparatus according to claim 1, further comprising a water tank for containing water in which the material is immersed, wherein the water tank is provided with a mount for fixingly supporting the sensor unit with respect to the material immersed in the water.

5. An apparatus according to claim 4, wherein the mount is capable of moving the sensor unit with respect to the surface of the material in the vertical direction.

6. An apparatus according to claim 5, wherein the mount is capable of moving the sensor unit at least in one axial direction in parallel with the surface of the material so that the sensor unit can scan the surface of the material.

7. An apparatus according to claim 1, wherein the probe is formed by a piezoelectric device, and a matching coil for matching the impedance of the piezoelectric device and that of the extractor is provided along a wave reception line between the piezoelectric device and the extractor.

8. An apparatus according to claim 1, wherein the extractor integrates the wave reception signals obtained in association with a plurality of transmissions of the ultrasonic pulse, and detects the reflected waves from the boundary between the first and the second layers of the material to be measured based on the integrated wave reception signals.

9. An apparatus according to claim 8, wherein the integrated wave reception signal is averaged by the number of integrations, the apparatus further comprising a display for displaying the waveform of the averaged wave reception signal.

10. An apparatus according to claim 1, wherein the extractor includes a gate movable along a time axis and extracts, out of the wave reception signal, a first wave component which passes the gate as the reflected wave from the boundary between the first and second layers of the material to be measured.

11. An apparatus according to claim 1, wherein the sensor unit comprises a local water immersion construction including:

a water reservoir having a water supply hole and an air-bubble discharge; and a surface which is placed in contact with the material and is sealed by a transparent sealing tape.

12. An apparatus according to claim 1, wherein said probe is oriented with respect to the material such that said waves enter said material at an angle of refraction of about 45 degrees.

13. An apparatus according to claim 1, wherein said probe is oriented with respect to the material so as to deliver said waves at an angle of incidence of about 19 degrees.

14. An apparatus according to claim 13, wherein an angle of refraction said waves in said material is about 45 degrees.

15. An apparatus for measuring a thickness of a layer, comprising:

a sensor unit including a probe for obliquely transmitting and receiving waves to and from the surface of a material to be measured having first and second layers with different grain sizes of grain particles in a depth direction;

an extractor for extracting, from a wave reception signal representing waves received by the probe, signals of waves that are reflected by the grain particles of the material; and a calculator for calculating a distance between the surface of the material and a change in the grain sizes of the grain particles based on the signals of waves; and the sensor unit having a local water immersion construction including:

a water reservoir having a water supply hole and an air-bubble discharge hole and having a surface which is in contact with the material and sealed by a transport sealing tape; and a holder of a transparent material having a fixing hole above and in communication with the water reservoir into which the probe is inserted to be fixed.

16. An apparatus for measuring a thickness of a layer, comprising:

a sensor unit including a probe for obliquely transmitting and receiving waves to and from a surface of a material to be measured having first and second layers with different grain sizes of grain particles in a depth direction;

an extractor for extracting, from a wave reception signal representing waves received by the probe, signals of waves that are reflected by the grain particles of the material;

a calculator for calculating a distance between the surface of the material and a change in the grain sizes of the grain particles based on the signals of waves;

the probe including a piezoelectric device;

a wave reception line connecting the piezoelectric device and the extractor; and a matching coil in series with the wave reception line for matching an impedance of the piezoelectric device and an impedance of the extractor.

17. An apparatus according to claim 16, wherein said piezoelectric device is oriented with respect to the material so as to deliver said waves at an angle of incidence of about 19 degrees.

18. An apparatus according to claim 17, wherein an angle of reaction of said waves in said material is about 45 degrees.

19. An apparatus according to claim 16, wherein said piezoelectric device is oriented with respect to the material such that said waves enter said material at an angle of refraction of about 45 degrees.

* * * * *